United States Patent [19]
Manalastas et al.

[11] Patent Number: 5,256,181
[45] Date of Patent: Oct. 26, 1993

[54] COATINGS WITH IONICALLY AND COVALENTLY CROSSLINKED SULFONATED POLYMERS

[75] Inventors: Pacifico V. Manalastas, Edison; Evelyn N. Drake, Bernardsville; Warren A. Thaler, Flemington; Edward N. Kresge, Watchung; Chester W. Elspass, Alpha, all of N.J. Albert J. Geiger, Fort Saskatchewan, Alberta, Canada; Vijay Swarup, Clinton, New Jersey

[73] Assignee: Exxon Research and Engineering Company, Florham Park, N.J.

[21] Appl. No.: 676,684

[22] Filed: Mar. 28, 1991

[51] Int. Cl.$^5$ .................. C05C 9/00; C08F 210/16; C05G 3/02; C05G 5/00
[52] U.S. Cl. .................. 71/28; 71/64.07; 71/DIG. 1; 504/101; 525/331.7
[58] Field of Search .......... 71/28, 64.07, 119, DIG. 1; 525/331.7

[56] References Cited

U.S. PATENT DOCUMENTS

| | | | |
|---|---|---|---|
| 4,526,951 | 7/1985 | Lundberg et al. | 526/240 |
| 4,701,204 | 10/1987 | Duvdevani et al. | 71/28 |
| 4,741,956 | 5/1988 | Thaler et al. | 71/64.02 |
| 4,988,377 | 1/1991 | Manalastas et al. | 71/28 |
| 5,110,486 | 5/1992 | Manalastas et al. | 252/8.551 |

*Primary Examiner*—Glennon H. Hollrah
*Assistant Examiner*—S. Mark Clardy
*Attorney, Agent, or Firm*—Jay Simon

[57] ABSTRACT

A composite comprising a urea substrate and ionically and covalently crosslinked, neutralized, sulfonated EPDM elastomeric coating encapsulating the urea.

9 Claims, 4 Drawing Sheets

COATINGS WITH IONICALLY AND COVALENTLY CROSSLINKED SULFONATED POLYMERS

FIELD OF THE INVENTION

The present invention relates to elastomeric coatings which are both ionically and covalently crosslinked which have improved barrier properties as well as improved physical properties wherein the elastomeric coating is formed from an organic solution of a sulfonated elastomeric polymer, an interpolymer complex of an anionic polymer and a cationic polymer, or a sulfonated polymer neutralized with a polycaprolactone polymer being characterized by the formula wherein $R_1$ or $R_2$ is an alkyl, cycloalkyl or aryl group; $R_3$, $R_4$ and $R_5$ are a hydrogen or alkyl, cycloalkyl, or aryl groups; m equals 1 to 20 and n equals 1 to 500; and a means of covalent crosslinking.

The present invention relates to controlled release fertilizers and particularly to fertilizer-pesticide compositions. The invention is more particularly directed to fertilizers and fertilizer-pesticide compositions to which thin films or ultrathin films or coatings of ionically and covalently crosslinked sulfonated polymers and interpolymer complexes have been applied as an improved controlled release agent. Related to this, the present invention is directed to methods for producing fertilizer and fertilizer-pesticide composites coated with ionically and covalently crosslinked sulfonated polymers and interpolymer complexes in addition to agricultural processes involving the use of such coated fertilizers and fertilizer-pesticide composites. In this regard, agricultural processes in which the fertilizer and fertilizer-pesticide composites coated with ionically and covalently crosslinked sulfonated polymers and interpolymer complexes in accordance with the present invention may be applied include processes for enhancing vegetation including plant growth stimulation and regulation as well as stimulation of seed germination.

DESCRIPTION OF PRIOR ART

Solids (e.g., substrates, pipes, slabs, sheets, etc.) can be protected from the external environment with the use of barrier or protective coating materials. For protection from water or moisture, polymer or organic materials are widely used. For cost effectiveness, however, these materials are generally applied as thin films. The thickness of the film depends upon the desired degree of water protection. The thicker the film the more likely that water penetration would be slowed down. In practice, applying an effective thin coating is difficult because of the various stresses tending to make the film discontinuous (e.g., film-rupture, pin holes). Films will rupture when a threshold stress is exceeded. The lateral stress tending to rupture a film is inversely proportional to an exponential power of the film thickness. The thinner the film, the more easily it will rupture.

In recent years, interpolymer complexes have received considerable attention in the literature due to their interesting and unique properties and their similarity to certain biological systems. In most instances, these complexes are formed by intimately mixing aqueous solutions containing high-charge density polyelectrolytes possessing opposite charge. When these polymer molecules meet in solution, the interaction between oppositely charged sites will cause the release of their associated counterions, forming the complex. The counterions are now free to diffuse into the bulk solution. Normally, phase separation occurs upon prolonged standing. These high-charge density complexes are not readily formed in organic solvents due to the insolubility of the individual components. Lower charge density complexes formed between lightly charged polymers such as sulfonated EPDM and styrene/vinyl pyridine copolymer, however, have been found to be soluble in certain organic solvents. These complexes have furthermore been shown to have superior film forming characteristics when covalently crosslinked.

The discovery of the superior film forming properties of ionically and covalently crosslinked sulfonated polymers and interpolymer complexes has made possible the extension of their use to coating applications, including controlled release products in agriculture (e.g., controlled release fertilizer). In controlled release fertilizer applications coatings of ionically and covalently crosslinked sulfonated polymers and interpolymer complexes will act as barriers to water soluble constituents of the fertilizer, shielding them from premature release in aqueous environments for periods ranging from several days to many months. Because of their unique barrier properties and physical properties sulfonated polymers and interpolymer complexes which are both ionically and covalently crosslinked can potentially be used to make cost effective controlled release fertilizers. The benefits obtained by the use of these coatings can include labor savings, increased crop yield, minimal leaching, increased nitrogen utilization efficiency and time savings. The amount of premium is proportional to the cost of coating used on the controlled release product. Therefore, it is of economic importance to use as little coating material as possible to make a desirable agricultural product. The amount of coating which should be applied on the controlled release product, however, is not only dictated by economic considerations, but also by the required performance. In most cases the performance requirements include the control of the release or dissolving property of the agricultural material, achievable with the application of coatings free of fine pinholes or defects. Herein lies the major problem in controlled release fertilizer, particularly with existing conventional coatings, because the thinner the coating or less coating material is applied the less likely that defect free coatings can be made. Thus, commercially available controlled release fertilizer products are with thick (>40 microns) coatings to yield acceptable performance (e.g., <20% release water soluble nutrient in seven days in water at 20° C.). As a consequence, these products are expensive and have found limited uses. With the discovery of ionically and covalently crosslinked sulfonated polymer and interpolymer complex coatings, however, the application of thin defect-free films on controlled release fertilizer can now be achieved; thus, its use presents a potential route for making affordable controlled release fertilizer.

The instant invention teaches that a solution of a sulfonated polymer, or an interpolymer complex of an anionic polymer and a cationic polymer where at least one of the two polymers is elastomeric with a covalent crosslinking means can meet many of the requirements for forming an improved thin film coating.

Coatings can be protective, decorative or special purpose and are usually applied at thicknesses of as high as 150 micrometers or thicker in order to provide the desired properties required of such coatings. Higher thicknesses are required in order to compensate for coating defects of for poor coating material properties.

Coatings in accord with this invention show improved properties may be applied as thin films having a thickness of 1-100 micrometers, with a preferred range of 2-40 micrometers. In order for such coatings to be functional the coating material should show improved barrier properties and be a continuous film with few or no defects.

Carbon, hydrogen, oxygen, nitrogen, phosphorus and sulphur are the primary elements essential to plant growth. Soils contain all of these elements in addition to other macro and micronutrients that enhance plant growth. Typically, however, such elements are seldom present in the soil in sufficient quantity or in forms that can support maximum plant productivity and yield. Therefore, fertilizers having specific chemical formulations and in pre-determined amounts must be added to enrich the soil to ensure maximum plant yield. The amount and form of the fertilizer added are pre-determined by chemically assaying the amount and availability of the required nutrient(s) in the soil, for example, as disclosed by Methods of Soil Analysis, 1982, Amer. Soc. Agronomy, Madison, Wis. Thus, appropriate fertilizer is added in amounts calculated to ensure the required plant yield based on known fertilizer response curves established by extensive agronomic testing for the particular plant and plant growth environment.

Fertilizers containing nitrogen, phosphorus, sulphur and/or potassium, by way of example, may be applied as solid granules or in liquid form. These primary fertilizers may be supplemented with certain trace elements such as copper, iron, manganese, zinc, cobalt, molybdenum, boron usually supplied as oxides or salts containing the elements in the cationic form. Suitable salts are, for example, sulphates, nitrates, chlorides, molybdates or borates. The difference between trace element deficiency and toxicity, however, is but a few parts per million as measured by the concentration of the element in the soil. Moreover, the efficiency of utilization of fertilizers, i.e., the percent uptake of the applied fertilizers is notoriously low. In this regard, chemical, biological and physical processes compete with the plant for the added fertilizer nutrients usually to the detriment of plant productivity. In addition, nitrogen fertilizers added to the soil may be leached into groundwater, chemically immobilized into clay minerals, chemically removed by volatilization of ammonia, biologically removed from the soil by denitrification to dinitrogen and nitrous oxide gases or immobilized into the active microbial biomass. These competing and simultaneous occurrences result in fertilizer use efficiency of nitrogen often being less than 50%. Thus, when 100 kg N/ha is added to the soil, the plant actually "sees" only 50 kg N/ha. Although most soils contain high levels of phosphorus, it is chemically immobilized as calcium phosphates, e.g., in soils of pH>7.0 or iron and aluminum phosphates, e.g., in soils of pH<5.0, and is thus not plant-available. Fertilizer phosphorus applied to these soils, however, is rapidly immobilized resulting in fertilizer use efficiencies seldom exceeding 30%.

If the release of nutrients from fertilizers could be controlled to more closely match the actual physiological requirements of the plant for the nutrient and if temporary or permanent losses of the fertilizer nutrients could be minimized if not eliminated, several advantages would accrue:

i) less fertilizer would be required to achieve the same plant yield;

ii) the same amount of fertilizer could be applied resulting in higher yields and concomitant lower per unit plant production costs;

iii) less water-soluble nitrogen would leach into groundwaters thus minimizing ground-water pollution; and/or iv) less nitrogenous gases would evolve into the atmosphere thus minimizing damage to the fragile ozone layer.

There are many applications for thickened or gelled solutions of polymers in organic liquids. There are also a number of physical and chemical techniques for preparing such systems. The present invention, however, is concerned with ionically and covalently crosslinked polymeric coatings having improved properties which have been found to be particularly suitable for application to agricultural products, such as fertilizers, pesticides, herbicides, insecticides, bacteriocides, fungicides, nematicide, sporicides, and the like, in addition to combinations thereof.

SUMMARY OF THE INVENTION

The present invention relates to a process for forming thin polymeric coatings which are both ionically and covalently crosslinked having improved barrier properties from an organic solution of (i) an organic liquid and a sulfonated polymer, or (ii) an interpolymer complex of a cationic polymer and an anionic polymer; and a means of covalent crosslinking.

The thin polymeric coatings are coated on vegetation enhancement, e.g., fertilizer or fertilizer-pesticide combinations. The process of the instant invention generally comprises an organic solution of a water insoluble sulfonated polymer or interpolymer complex with a crosslinking agent which is not activated until a temperature of 40° C. is obtained; coating the organic solution of the water insoluble sulfonated polymer or interpolymer complex and the crosslinking agent onto a substrate and subjecting the coated substrate to a temperature of at least 40° C. to activate the crosslinking agent thereby covalently crosslinking the sulfonated polymer or interpolymer complex. An alternative process comprises coating an organic solution of the water insoluble sulfonated polymer or interpolymer complex on the substrate and subsequently subjecting the coated substrate to an electron beam thereby covalently crosslinking the water insoluble sulfonated polymer or interpolymer complex. A still alternate process comprises coating a substrate with an organic solution of the water insoluble sulfonated polymer or interpolymer complex and subsequently contacting the coated substrate with a vapor or solution of sulfur monochloride thereby forming a covalently crosslinked water insoluble sulfonated polymer or interpolymer complex. It is contemplated within the scope of this invention that any one or all three of these processes in conjunction could be used to crosslink the water insoluble sulfonated polymer or interpolymer complex. It is also contemplated that the water insoluble sulfonated polymer or interpolymer complex could be covalently crosslinked either in solution or as a solid to form a formed polymeric article by any one of the aforementioned processes.

In general, the present invention, therefore, relates to coating vegetation enhancement agents, such as fertilizers and fertilizer-pesticide combinations, with thin or ultra-thin coatings of ionically and covalently crosslinked sulfonated polymers or interpolymeric complexes to result in controlled release fertilizers and fertilizer-pesticide combinations having improved barrier properties, as well as agricultural processes involving methods of using fertilizers and fertilizer-pesticide combinations coated with crosslinked sulfonated polymers or interpolymeric complexes in accordance with the present invention so as to decrease dissolution of soluble fertilizer components, increase fertilizer use efficiency and substantially decrease losses of the added fertilizer from the plant growth medium due to biological, chemical, or physical processes competing with the plant for the said nutrients.

DETAILED DESCRIPTION OF THE INVENTION

The component materials of the instant invention generally include a water insoluble sulfonated polymer or interpolymer complex dissolved in an organic solvent system to form a solution with a concentration level of 0.1 to 20 weight percent, wherein the solution can contain a covalent crosslinking agent which is activated at a minimal temperature of about 40° C., or alternatively, the polymeric coating can be crosslinked by a post coating crosslinking means. The solvent system comprises an organic solvent with or without a polar cosolvent, such as alcohols, amines, or ammonia. The solvent can be an organic liquid which is capable of dissolving the polymeric backbone. A cosolvent may be needed to break up associated domains resulting from aggregation of ionic species.

The water insoluble, ionically crosslinked, sulfonated polymers of the instant invention will comprise from about 4 to about 200 milliequivalents of pendant sulfonated groups per 100 grams of polymer, more preferably from 10 to 100 meq. pendant sulfonated groups. In most instances, the sulfonated polymers utilized in the instant invention are acids or are neutralized with transition elements selected from Groups IVA, VA, VIA, VIIA, VIIIA, IB and IIB of the Periodic Table of Elements and lead, tin and antimony, as well as ammonium and amine counterions. Sulfonated polymers which are subject to the process of the instant invention include both plastic and elastic polymers which contain unsaturation in the polymeric backbone. Specific polymers include sulfonated polystyrene, sulfonated methylstyrene, sulfonated copolymer of styrene-t-butyl styrene, styrene-methyl styrene, styrene-isobutylene, sulfonated ethylene copolymers, sulfonated atactic propylene polymers and propylene copolymers, sulfonated styrene/acrylonitrile copolymers, sulfonated styrene/methyl methacrylate copolymers, sulfonated block copolymers of styrene/ethylene oxide, acrylic acid copolymers with styrene, sulfonated isobutylene isoprene copolymers (Butyl rubber), sulfonated ethylene-propylene terpolymers, sulfonated isoprene styrene or butadiene styrene-block copolymers and the sulfonated hydrogenated block copolymers. The preferred sulfonated polymers of the instant invention are ethylene-propylene terpolymers, Butyl rubber and polystyrene, wherein the ethylene-propylene terpolymers and polystyrene are most preferred.

Neutralization of the cited polymers with appropriate metal hydroxides, metal acetates, metal oxides, or ammonium hydroxide, etc., can be conducted by means well known in the art. For example, the sulfonation process as with Butyl rubber, containing a small 0.3 to 1.0 mole percent unsaturation, can be conducted in a suitable solvent, such as toluene, with acetyl sulfated as the sulfonated agent, such as described in U.S. Pat. No. 3,836,511, incorporated herein by reference. The resulting sulfonic acid derivative can then be neutralized with a number of different neutralization agents, such as sodium phenolate and similar metal salts. The amounts of such neutralization agents employed will normally be stoichiometrically related to the amount of free acid in the polymer, plus an unreacted agent which is still present. It is preferred that the amount of neutralizing agent be equal to the molar amount of sulfonating agent originally employed plus 10 percent more to ensure full neutralization. The use of more of such neutralization agent is necessary to effect at least 50 percent neutralization of the sulfonic acid groups present in the polymer, preferably at least 90 percent, and most preferably essentially complete neutralization of such acid groups should be effected.

Thus, the degree of neutralization of said sulfonated groups may vary from 0 (free acid form) to greater than 100 mole percent, preferably 50 to 100 mole percent. With the utilization of neutralized sulfonated in this instant invention, it is preferred that the degree of neutralization be substantially complete, that is, with no substantial free acid present and without substantial excess of the base, other than that needed to ensure neutralization. The neutralized sulfonates possess greater thermal stability compared to their acid form. Thus, it is clear that the polymers which are normally utilized in the instant invention comprise substantially neutralized pendant groups and, in fact, an excess of the neutralizing material may be utilized without defeating the objects of the instant invention.

The sulfonated polymers of the instant invention may vary in number average molecular weight from 1,000 to 10,000,000, preferably 5,000 to 1,000,000, most preferably from 10,000 to 600,000. These polymers may be prepared by methods known in the art, for example, see U.S. Pat. No. 3,642,728, hereby incorporated by reference.

The preferred sulfonated polymers for use in the instant invention, which are sulfonated ethylene propylene terpolymers, may be prepared by the procedures described in U.S. Pat. No. 3,870,841, hereby incorporated by reference.

The sulfonated polymers of the instant invention may be neutralized prior to incorporation into the organic solvent or by neutralization of the acid form in situ. For example, preferably the acid derivative is neutralized immediately after preparation. For example, if the sulfonation of an EPDM terpolymer is conducted in solution, then the neutralization of that acid derivative can be conducted immediately following the sulfonation procedure. The neutralized polymer may then be isolated by means well known to those skilled in the art, i.e., coagulation, steam stripping or solvent evaporation, because the neutralized polymer has sufficient thermal stability to be dried for employment at a later time in the process of the instant invention. It is well known that some unneutralized sulfonic acid derivatives do not possess good thermal stability and the above operations avoid that problem.

The concentration of the neutralized sulfonated polymer in the solution is about 0.1 to about 20 weight percent, more preferably about 0.5 to about 10, and most preferably about 0.5 to about 6.0. As discussed above, a variety of polymer backbones will display the desirable properties discovered in this invention.

Specific examples of the organic liquids to be employed with the various types of polymers are:

| Polymer | Organic Liquid |
|---|---|
| sulfonated polystyrene | benzene, toluene, ethyl benzene, methylethyl ketone, xylene, styrene, ethylendichloride, methylene chloride. |
| sulfonated poly-t-butyl-styrene | benzene, toluene, xylene, ethyl benzene, styrene, t-butyl styrene, aliphatic oils, aromatic oils, hexane, heptane, decane, nonane. |
| sulfonated ethylene-propylene terpolymer | pentane, aliphatic and aromatic solvent oils, such as Solvent "100 Neutral", "150 Neutral" and similar oils, benzene diesel oil, toluene, xylene, ethyl benzene, pentane, hexane, heptane, octane, isooctane, nonane decane, aromatic solvent, ketone solvents. |
| sulfonated styrene-methyl methacrylate copolymer | dioxane, halogenated aliphatics, e.g., methylene chloride, tetrahydrofuran. |
| sulfonated polyisobutylene | saturated aliphatic hydrocarbons, diisobutylene, triisobutylene, aromatic and alkyl substituted aromatic hydrocarbons, n-butyl ether, n-amyl ether, methyl oleate, aliphatic oils, oils predominantly paraffinic in nature and mixtures containing naphthenic hydrocarbons. "Solvent 100 Neutral", "Solvent 150 Neutral" and all related oils, low molecular weight polymeric oils such as squalene, white oils and process oils having 60 percent or less aromatic content. |
| sulfonated polyvinyl toluene | toluene, benzene, xylene, cyclohexane, ethyl benzene, styrene, methylene chloride, ethylene dichloride. |

In order to reduce the viscosity of organic hydrocarbon solution of the sulfonated polymer so as to be able to employ the organic hydrocarbon solution in a casting process, a polar cosolvent may be added to the organic hydrocarbon solution of the sulfonated polymer to solubilize the pendant ionomeric groups. The polar cosolvent will have a solubility parameter of at least 10.0, more preferably at least 11.0, and may comprise from 0.01 to 15.0 weight percent, preferably 0.1 to 5.0 weight percent, of the total mixture of organic liquid, water insoluble ionomeric polymer and polar cosolvent.

Normally, the polar cosolvent will be a liquid at room temperature, however, this is not a requirement. It is preferred, but not required, that the polar cosolvent be soluble or miscible with the organic liquid at the levels employed in this invention. The polar cosolvent is selected from the group consisting essentially of alcohols, amines, ammonia, di- or tri-functional alcohols, amides, acetamides, phosphates, or lactones and mixtures thereof. Especially preferred polar cosolvents are aliphatic alcohols, such as methanol, ethanol, n-propanol, ispropanol, 1.2-propane diol, monoethyl ether of ethylene glycol and n-ethylformamide, and methyl isobutyl carbinol.

In general, the inter polymer complexes are formed from the interaction in solution of a water insoluble anionic, sulfonated polymer and a water insoluble cationic or base containing copolymer, such as styrene/vinyl pyridine copolymer.

The water insoluble cationic or base containing copolymer will comprise from about 0.5 to 50 mole percent cationic or basic groups situated along the chain backbone or, alternatively, the cationic or basic group content will range from about 4 meq. to about 500 meq. per 100 grams of polymer. The cationic or basic groups may be conveniently selected from primary, secondary and tertiary amine groups contained in polymerizable monomers. Included in these categories are pyridine, anilines, pyrroles, amides and other basic polymerizable ammonia derivatives. Specific polymers include styrene-4-vinylpyridine, styrene-2-vinylpyridine, b-Butyl styrene-4-vinylpyridine, ethylene-4-vinylpyridine copolymers, propylene-4-vinylpyridine copolymers, acrylonitrile-4-vinylpyridine, methyl methacrylate-4-vinyl pyridine copolymers, block copolymers and ethylene oxide/4-vinylpyridine, acrylic acid-4-vinylpyridine copolymers, ethylene-propylene-4-vinylpyridine terpolymers, isoprene-4-vinylpyridine, 4-vinyl pyridine-elastomers copolymers and the like. The preferred base-containing polymers of the instant invention are styrene and 4-vinylpyridine and ethylene-propylene terpolymers with grafted 4-vinylpyridine. The former polymers are the preferred species.

The copolymer of styrene/vinyl pyridine is typically formed by the emulsion copolymerization of freshly distilled styrene and vinylpyridine monomers. This method of copolymerization is generally known to those well versed in the art. As noted previously, solution or suspension techniques may also be used to prepare those base-containing polymeric materials.

The interpolymer complex of the neutralized sulfonated polymer and the copolymer of styrene/vinyl pyridine is formed by forming a first solution of the neutralized sulfonated polymer in the previously described solvent system. A second solution of the copolymer of styrene/vinyl pyridine is formed by dissolving the copolymer of styrene/vinyl pyridine in an aromatic solvent, such as xylene or toluene. The concentration of the neutralized sulfonated polymer in the first solution is about 0.1 to about 20 weight percent, more preferably about 0.5 to about 10, and most preferably about 0.5 to 6. The first solution of the neutralized sulfonated polymer and the second solution of the copolymer of styrene/vinylpyridine are mixed together, thereby permitting the interaction of the neutralized sulfonated polymer and the copolymer of styrene/vinylpyridine to form the water insoluble interpolymer complex. Alternatively, both polymers can be dissolved simultaneously in the same solvent system. The molar ratio of polymer to nitrogen in the copolymer of styrene/vinylpyridine in the interpolymer complex is about 0.1 to about 20, more preferably about 0.5 to about 10, and most preferably about 1 to about 5. The concentration of the interpolymer complex in the hydrocarbon organic liquid is about 0.1 to about 20 weight percent, more preferably about 0.1 to about 10, and most preferably about 0.5 to about 6.

We have found that a very important factor in determining the strength of the interaction between the cation or base containing polymer and the sulfonate-containing polymer is the nature of the counterion. There are, broadly speaking, three major classes of such counterions. The first class, which are less preferred, are those metals of Group IA and Group IIA, which include Li, Na, K, etc., Be, Mg, Ca, etc. We have found that these species do not interact as strongly with amine groups as the more preferred species described below. Those metals are commonly defined as members of the transition elements (see chemical text: *Chemical Principles and Properties*, by M. J. Sienko and R. A. Plane, McGraw Hill Book Co., 1974, page 19). These metal cations are best exemplified by zinc and interact strongly with pyridine and similar amines. As a consequence, a zinc neutralized sulfonated polymer interacts much more strongly with a styrene/vinylpyridine copolymer than does a magnesium or sodium neutralized system. It is for this reason that the transition elements are preferred, with zinc, copper, iron, nickel and cobalt being especially preferred. We also include antimony and lead as suitable cations.

A third species which is preferred is the free acid of the sulfonated polymer, which will also interact with amine-containing polymers. In this latter case, it is clear that the interaction is a classic acid-base interaction, while with the transition metals a true coordination complex is created, which is due to the donation of the electron pair of the nitrogen element. This distinction is a very important one and sets these complexes apart from classic acid-base interactions. The surprising observation is that such coordination complexes can form in such extreme dilution insofar as interacting groups are concerned and that they are apparently formed so far removed from their expected stoichiometry (based on small molecule analogs).

As discussed above, a variety of polymer backbones will display the desirable properties discovered in this invention and are summarized as follows:

| Sulfonate Polymer | Cationic or Basic Polymer |
| --- | --- |
| Sulfo-EPDM | Styrene/Vinylpyridine Copolymer |
| Sulfonated Isoprene Copolymers | Vinylpyridine/Styrene/Butadiene Terpolymers |
| Sulfonated SBR Polymers | Isoprene/Vinyl Pyridine Copolymer |
| Sulfonate Butadiene Polymers | Ethylacrylate/Vinylpyridine Copolymer and Alkyl Acrylate |
| Sulfonated Butyl | Copolymers with Vinyl Pyridine where the Alkyl group varies in carbon number from 1 to 18 |
| Sulfonated Acrylate and Methacrylate Copolymers | |
| Sulfonated Block Copolymers | Methyl Methacrylate/Vinyl Pyridine Copolymer and Alkyl Methacrylate copolymers with |

| Sulfonate Polymer | Cationic or Basic Polymer |
| --- | --- |
| | Vinylpyridine wherein the number of carbon groups in the alkyl groups varies from 1 to 18 carbon atoms |
| | Butadiene/Vinylpyridine Copolymer |
| | Propylene/Vinylpyridine Block Copolymer |
| | Ethylene/Vinylpyridine Block Copolymer t-Butyl |
| | Styrene/Vinylpyridine Copolymers |
| | Vinylpyridine Copolymers with alpha-beta ethylenically unsaturated copolymers or terpolymers |

The amount of vinylpyridine in the amine-containing polymer can vary widely, but should range from less than 50 mole percent down to at least 0.5 mole percent.

Preferably, the amine content in the cationic or basic polymer is expressed in terms of basic nitrogen. In this respect, the nitrogen content of amides and similar non-basic nitrogen functionality is not part of the interacting species.

A minimum of three basic or cationic groups must be present on the average per polymer molecule and the basic or cationic nitrogen content generally will range from 4 meq. per 100 grams of polymer up to 500 meq. per 100 grams. A range of 8 to 200 meq. per 100 grams is preferred.

The polymeric coatings of the instant invention are formed by applying the organic solution of the sulfonated polymer or interpolymer complex and optionally the covalent crosslinking agent over the substrate at an ambient temperature of 10° C. -70° C., but at a temperature lower than the activation temperature of the covalent crosslinking agent, by either dip coating or spray coating or with the use of other techniques for thin spreading (such as brushing). The organic solvent system is then permitted to evaporate with or without the aid of forced drying gas, such as air or nitrogen gas. This step is called the drying process. The drying gas temperature can be from ambient temperature up to the boiling point of the organic solvent system. Preferably the temperature of the drying gas is between 20° C. to 100° C. The most preferred temperature of the drying gas should be from about 50° C. to about 70° C. for fast evaporation of the organic solvent system. After drying the thickness of the applied coating should be about 1 micrometer to about 100 micrometers. Most preferred, the coating thickness should be about 2 to about 40 micrometers for both performance and economic reasons. To control the thickness of the applied coating, the solution concentration of the sulfonated polymeric is applied at 0.5 to 6 weight percent. The coating solution of the sulfonated polymer or interpolymer complex can be applied in single or multiple layers, depending on the desired coating thickness. In any instance, the organic solvent system is evaporated after each layer application. The sulfonated polymer coating can be applied over the substrate of interest or over a previous coating. In the latter case, such practice can modify or improve the performance of the coated system.

Covalent crosslinking of the above mentioned polymers can be carried out with a variety of common vulcanization formulations involving crosslinking peroxides, carriers for crosslinking peroxides, accelerators and sensitizers.

Examples of peroxide crosslinking agents include acetyl cyclohexane sulphonyl peroxide, bis (2-ethylhexyl) peroxydicarbonate, bis (4-tert butyl cyclohexyl) peroxydicarbonate, di-cyclohexyl peroxydicarbonate, di-n-propyl peroxydicarbonate, di-n-butyl peroxydicarbonate, dicetyl peroxydicarbonate, disecbutyl peroxydicarbonate, di-isopropyl peroxydicarbonate, tert butyl peroxyeodecanoate, bis (2,4-dichlorobenzoyl) peroxide, tert butyl peroxypivalate, bis (ortho-methyl benzoyl) peroxide, bis (orthomethylbenzoyl) peroxide, bis (3,5,5-trimethyl hexanoyl) peroxide, dilauaryl peroxide, didecanoyl peroxide, di-octanoyl peroxide, di-proprionoyl peroxide, di-benzoyl peroxide, tert butyl peroxy-2-ethylahexanoate, tert butyl peroxy diethylacetate, tert buty peroxy isobutyrate and others like them.

Possible carriers for the peroxide are contemplated to be calcium carbonate, clay, EVA copolymer masterbatch, EPDM-masterbatch, silicon oil, plasticizer as well as organic solvents.

Accelerators are contemplated to include thiazoles, sulfenamides, thiurams, dithiocarbamates, guaridines and thioureas.

Sensitizers are contemplated to include trialkyl cyanurate, trialkyl isocyanurate, trimethylolpropane trimethacrylate, ethylene glycol dimethacrylate.

The concentration of the covalent crosslinking agent in the organic solution or carrier is about 0.1 to about 20 weight percent, more preferably about 0.15 to about 15 weight percent and most preferably about 0.17 to about 10 weight percent. The curing of the coating of the sulfonated polymer or interpolymer complex with the covalent crosslinking agent occurs during the aforementioned drying step of the process at temperatures above 40° C..

In the process of curing the sulfonated polymer or interpolymer complex coating with an electron beam, the coating is first dried in the aforementioned drying step of the process. The dried sulfonated polymer or interpolymer complex coating is cured by exposure to an electron beam radiation at ambient temperature for a sufficient period of time (10 to 60 minutes) to cause covalent crosslinking, wherein the electron beam is 1 to 50 Mrad, preferably 2 to 25, and most preferably 5 to 20.

Where sulfur monochloride is employed as the crosslinking agent, there are several approaches which may be used to crosslink the coating. In a first embodiment, the substrate particles coated with the dried sulfonated polymer or interpolymer complex coating is covalently crosslinked by exposing the coated particles to a saturated vapor of sulfur monochloride at ambient temperature for a sufficient period of time, 1 hour to 48 hours, more preferably 2 hours to 36 hours, and most preferably 10 hours to 30 hours, to cause covalent crosslinking. The coated polymer particles may be exposed to vapor by placing them on a screen in a desiccator or in a packed column and exposing the particles to the vapor for a period of time sufficient to cause covalent crosslinking of the sulfonated polymer.

In another variation of this process, the coated particles may be covalently crosslinked by contact with a solution of sulfur monochloride in an organic solvent selected from the group consisting of aliphatic, aromatic and halogenated hydrocarbons. The concentration of sulfur monochloride in the solution should be about 1 to about 50 weight percent, more preferably 2 to 40 weight percent, and most preferably 3 to 30 weight percent. The amount of sulfur monochloride solution used to cross-link the polymer contains enough sulfur monochloride to equal about 1.0 to about 20 weight percent of the weight of polymer in the coating, more preferably about 2.0 to about 15 weight percent and most preferably about 3.0 to about 12 weight percent of the polymer. The solution can be sprayed onto the coated particles by any means which ensures uniform distribution and then the solution is permitted to evaporate.

In yet another embodiment, crosslinking with sulfur monochloride may be carried out by direct addition of sulfur monochloride to the sulfonated polymer solution immediately prior to spray coating. The amount of sulfur monochloride added may range from the weight of about 1.0 to about 20 weight percent based on the weight of the sulfonated polymer to which it is added, more preferably about 2.0 to about 15 weight percent and most preferably about 3.0 to about 12 weight percent of the polymer. The spray coating and drying process is then carried out as described above.

The ionically and covalently crosslinked sulfonated polymer or interpolymer complex coating can be used as a barrier to create desired slow release for many types of fertilizers, micronutrients or other solid materials either individually and/or in mixtures, suitable for purposes of the present invention including by way of example:

MACRONUTRIENTS

Nitrogen, for example provided by:
Ammonium sulphate
Ammonium chloride
Ammonium nitrate
Diammonium phosphate
Ammonium phosphate nitrate
Monoammonium phosphate
Ammonium phosphate sulphate
Sodium nitrate
Potassium nitrate
Calcium nitrate
Urea
Ammonium nitrate-calcium carbonate mixture
  Potassium, for example provided by:
Potassium nitrate
Sulphate of potash
Muriate of potash
Potassium metaphosphate
  Phosphorous, for example provided by:
Ammonium phosphate nitrate
Ammonium phosphate sulphate
Monoammonium phosphate
Diammonium phosphate
Single superphosphate
Triple superphosphate
Potassium metaphosphate
  Sulfur, for example provided by:
Ammonium sulphate
Ammonium phosphate sulphate
Sulphate potash
Calcium sulfate
Ammonium bisulphite
Ammonium phosphate
Ammonium polysulphide
Ferrous sulphate
Gypsum
Kalinite
Leonite
Magnesium sulphate
Polyhalite Pyrite
Schoenite
Sodium sulphate
Sulphur
Sulphur dioxide
Single superphosphate
Urea sulphur
Zinc sulphate
  Calcium, for example provided by:
Calcium nitrate
Calcium sulfate
Calcium chloride

MICRONUTRIENTS

Boron as:
Borax (sodium tetraborate decahydrate)
Sodium tetraborate pentahydrate
Sodium tetraborate pentaborate
Colemanite
  Copper as:
Cupric oxide
Curous oxide
Cupric sulphate nonahydrate
Ferrous sulphate heptahydrate
  Manganese as:
Manganous carbonate
Manganous oxide
Manganous-manganic oxide
Manganous sulphate monohydrate
  Molybdenum as:
Ammonium molybdate
Sodium molybdate (anhydrous)
Molybic oxide
  Zinc as:
Calcinated zinc concentrate
Zinc carbonate
Zinc oxide
Zinc sulphate monohydrate Conventional slow release fertilizers may also be coated with the ionically and covalently crosslinked sulfonated polymer or interpolymer complex in accordance with the present invention, such as:

| | |
|---|---|
| Sulphur coated urea | Glycouril |
| Isobutylidene diurea | Magnesium ammonium |
| Crotonylidene diurea | phosphate (Mag Amp) |
| Urea formaldehyde | Guanyl urea sulphate |
| Trimethylene tetraurea | (GUS) |
| Oxamide | Guanyl urea phosphate |
| Cyanuric acid | (GUP) |
| Ammeline | Thiourea |
| Ammedlide | Phenylurea |

Urease or nitrification inhibitors can be included with the fertilizers. Examples of such inhibitors include urease inhibitors such as phenyl phosphoro-diamidate (PPD) and N-)n-butyl) thiophosphoric triamide (NBPT) and nitrification inhibitors such as N-serve (2-chloro-6-trichloromethyl pyridine) and dicyandiamide (DCD).

The present invention is particularly suitable for combinations of the aforementioned fertilizers with any pesticide although the present invention can be practiced with fertilizers and/or pesticides alone. Examples of suitable pesticides include herbicides such as triallate and trifluralin; insecticides such as carbonfuvan and aldicarb; fungicides such as captan and benomyl; rodenticides such as warfarin and chlorophacinone; nematocides such as O-ethyl S,S-dipropyl phosphorodithioate and O,O-diethyl O-(P-methyl sulfinyl) phenyl phosphorathioate; ascaricides such as kelthane and plictran; and bacteriocides such as stryptomycin and terronycin.

The plant growth media to which the fertilizers and fertilizer-pesticide composites coated in accordance with the present invention may be applied include liquid cultures, i.e., hydroponics, soil-less cultures and any mixture of sand, vermiculite, peat, perlite, or any other inert or relatively inert support, and soils which can be either irrigated or rainfed soils.

The seeds or plants envisioned to be fertilized by the instant invention include any species falling in the Plant Kingdom. Examples of such include the following: cereals such as wheat, maize (corn), rice, barley, oats; grasses such as bluegrass, fiscues, bromegrass (for forage, seed and/or turf production); legumes such as alfalfa, soybeans, bean, peas, lentils; oil seeds such as canola, palm, cotton, olive, flax; vegetables such as potatoes, lettuce, celery, carrot, onion, tomatoes, peppers; other broadleaf plants such as mint; coniferous and deciduous trees and shrubs; and flowers such as chrysanthemum, roses and tulips.

It should be understood, however, that the inclusion of herbicides with fertilizers coated with ionically and covalently crosslinked sulfonated polymers or interpolymer complexes are not inconsistent with the term vegetation enhancement agent which is intended to be applied to the desired or target plant. The fact that herbicide may kill undesired vegetation does not diminish its role as a vegetation enhancement agent for others, particularly the vegetation for which the fertilizer is intended.

The previously listed fertilizers and pesticides, either individually and/or in mixtures, may be coated with ionically and covalently crosslinked sulfonated polymers or interpolymer complexes in accordance with the present invention. In this regard, the substrate of the vegetation enhancement agent for purposes of the present invention may be a member selected from the group consisting of macronutrients, micronutrients, nitrogen fertilizers including inhibitors of urease, nitrogen fertilizers including inhibitors of nitrification activity, slow release fertilizers, and pesticides, in addition to mixtures of a plurality of each of the macronutrients, micronutrients, nitrogen fertilizers including inhibitors of urease, nitrogen fertilizers including inhibitors of nitrification activity, slow release fertilizers and pesticides, as well as mixtures of members from each group of macronutrients, micronutrients, nitrogen fertilizers including inhibitors of urease, nitrogen fertilizers including inhibitors of nitrification activity, slow release fertilizers and pesticides. In addition, the fertilizers and fertilizer/pesticide combinations coated with ionically and covalently crosslinked sulfonated polymer or interpolymer complex in accordance with the present invention may be mixed with non-coated fertilizers and/or pesticides of the same or different composition. In this regard, the non-coated member may be selected from the group consisting of macronutrients, micronutrients, nitrogen fertilizers including inhibitors of urease, nitrogen fertilizers including inhibitors of nitrification activity, slow release fertilizers and pesticides in addition to mixtures of a plurality of each of the groups of vegetable enhancement agents as well as mixtures of one or more members of each of the previously mentioned groups. When this is the case, the fertilizer or fertilizer/pesticide combination coated with the ionically and covalently crosslinked sulfonated polymer or interpolymer complex in accordance with the present invention may comprise 5 to 95% by total weight of the mixture or the non-coated vegetation enhancement agent may comprise 5% to 95% by total weight of the mixture.

The plant growth media to which the fertilizers and fertilizer-pesticide composites coated in accordance with the present invention may be applied include liquid cultures, i.e., hydroponics, soil-less cultures and any mixture of sand, vermiculite, peat, perlite, or any other inert or relatively inert support, and soils which can be either irrigated or rainfed soils.

A variety of substrates which are discrete particulate solids may be encapsulated to form advantageous products. In some applications substrates are required to be released in a slow or controlled manner in given environments. Examples include: fertilizers, micronutrients, coated seeds, synthetic reagents or catalysts, pharmaceuticals and drugs. Substrates can also be modified by encapsulation in cases where their solid surfaces need to be more compatible when they are added to other materials. Examples are engineering plastics, adhesives or rubbers with incorporated filler particles, such as ground lime, carbon black or titanium dioxide, or zinc oxide.

The vegetation enhancement agent, i.e., fertilizer or fertilizer/pesticide combination, to which the present invention is applicable is preferably in a substantially solid form, i.e., particles, having a dimension, and preferably a major dimension, within the range of about 1.0 to 10.0 mm. Preferably, the fertilizer particles are granules having a diameter within the range of about 1.0 to 6.0 mm and most preferably about 1.0 to about 3.5 mm. Commercial fertilizer granules typically have a diameter of about 2.3 mm, although particles, such as granules having a diameter as large as about 6 mm, have been found to be useful, particularly for purposes of aerial application, for example, used in the forestry industry.

Although the present invention has been described in connection with coating a vegetation enhancement agent, such as fertilizers/pesticide combinations, with a layer or film of crosslinked interpolymer complex, it should be understood that the present invention may also be used to coat a previously coated fertilizer or fertilizer/pesticide combination, such as conventional slow release fertilizers. Alternatively, fertilizers coated with ionically and covalently crosslinked sulfonated polymer or interpolymer complex in accordance with the present invention may also be coated with a conventional slow release coating, to which additional applications of the ionically and covalently crosslinked sulfonated polymer or interpolymer complex films or coatings in accordance with the present invention may be applied. Thus, a multiple-coated fertilizer or fertilizer/pesticide combination may be produced in accordance with the present invention. In this regard, however, it is preferred that the film or coating of the ionically and covalently crosslinked sulfonated polymer or interpolymer complex be either in direct contact with the vegetation enhancement agent, or form the exterior surface of the coated composite.

The present invention is also directed to agricultural processes, such as those for the enhancement of vegetation or vegetable matter. As used herein, vegetable matter is meant to be a division of nature comprising the plant kingdom as distinguished from matter of animal and mineral origin. Thus, vegetable matter includes seeds and plants, including seedlings, young plants, or any organ from which a plant can be generated, including naturally promulgated vegetable matter in addition to genetically engineered vegetable matter.

More specifically, the process of the present invention is directed to the stimulation of the germination and growth of a seed or a plant, including seedlings, young plants or any organ from which a plant can be generated, which involves the step of exposing the vegetable matter, e.g., the seed or plant, and/or the plant growth medium, i.e., soil, water and the like, either before, simultaneously with, or after the addition of the seed or plant to the plant growth medium to a fertilizer and/or fertilizer-pesticide combinations having a thin layer of a crosslinked interpolymer complex coated thereon.

In addition, the process also relates to the intimate admixing of fertilizer, such as urea, ammonical, phosphorus and/or sulphur fertilizers, alone or combined with pesticides, with a seed or plant, or other vegetable matter, as defined herein, without damage to the same in a plant growth medium which involves the steps of:

1) admixing or otherwise contacting a fertilizer, preferably in solid granular form, having a thin ionically and covalently crosslinked sulfonated polymer or interpolymer complex film or coating thereon with a seed or plant;

2) placing such a fertilizer in close proximity to the seed or plant with or without a separation of time between the fertilizer and seedling steps.

In this regard, it has been discovered that fertilizers with thin films or coatings of ionically and covalently crosslinked sulfonated polymers or interpolymer complexes, for example urea and ammonium sulfate, can be placed with the seed at the rate exceeding 25 kgN/ha without damage to the seed, seedlings, or young plants. Thus, the fertilizer and fertilizer/pesticide combinations having thin films or coatings of ionically and covalently crosslinked sulfonated polymer or interpolymer complexes have been found to be extremely effective in stimulating seedling emergence and early plant growth by permitting the placement of urea fertilizers with the seed at the time of planting. It has been discovered that the thin ionically and covalently crosslinked sulfonated polymer or interpolymer complexes film or coating slows the release of urea and ammonium to a sufficient extent to prevent burning of the seed or young seedling to which such a fertilizer is applied. In contrast to conventional slow release fertilizers, for example, urea coated with a thin film of ionically and covalently crosslinked sulfonated polymer or interpolymer complexes in accordance with the present invention can be applied to the plant growth media at a rate in excess of 25 kgN/ha without raising the pH of the seed in the plant media a sufficient extent to burn the seed and prevent emergence.

Although phosphorous fertilizers are routinely seed-placed and have been found to be effective in stimulation of emergence and yield, known as the "pop-up" effect, seed-placing has not believed to have been possible with conventional ammonical nitrogen fertilizers prior to the development of the ionically and covalently crosslinked interpolymer complexes coated fertilizers and fertilizer/pesticide combination in accordance with the present invention. Thus, the crosslinked interpolymer complexes coated fertilizers and fertilizer/pesticide combinations in accordance with the present invention have been found to be particularly advantageous in promotion of emergence, and early growth stimulation of seedlings, while permitting placement of the fertilizer with the seed.

Although the coated fertilizer of the present invention has been found to be particularly advantageous in permitting the introduction of nitrogen fertilizers and fertilizer/pesticide combinations simultaneously into the soil with the seed so as to stimulate emergence of seedlings and the growth of plants, fertilizers coated in accordance with the present invention may also preferably contain a source of sulfur and phosphorous, in which case, the fertilizer may be applied so as to supply nitrogen at a rate in excess of 25 kg/ha, sulfur in excess of 15 kg/ha, and phosphorous at a rate in excess of 30 kg/ha without burning the seeds or preventing subsequent emergency of the seedlings.

The present invention, therefore, is particularly suitable for replacing split or multiple applications of uncoated fertilizers to ensure that the available plant nutrient matches the physiological need of the crop for the same. In this regard, plants so not require all of their nitrogen at one time; for example, wheat requires over 35% of its nitrogen between booting and the soft touch stage. Typically uncoated fertilizers are applied in split applications at key physiological plant growth stages such as tillering, stem elongation, booting and seed filling to ensure that the nitrogen is available to the plant as required. Controlled release nitrogen, therefore, is effective in replacing split fertilizer applications. Controlled release nitrogen holds the nitrogen in a form until the nitrogen is needed by the plant. It has been discovered that the sulfonated polymer coated fertilizer and fertilizer/pesticide combinations in accordance with the present invention are particularly suitable for introduction with the seed and/or into the plant growth median during a single agricultural step so as to eliminate the need for post emergence application of the fertilizer.

The fertilizer and fertilizer/pesticide combination coated with thin films of ionically and covalently crosslinked sulfonated polymer or interpolymer complexes in accordance with the present invention, however, may also be introduced into the soil prior to a subsequent planting of the seeds. For example, the coated fertilizer of the present invention may be introduced into the soil in the Fall of a year prior to planting wheat in the Spring of the following year, without appreciable loss of nutrients. Thus the coated fertilize of the present invention may be formulated so as to supply nitrogen at a sufficient rate and timing of release to satisfy the physiological need for nitrogen of the wheat beginning in the Spring of the year when the wheat is sown through to the growing season. The coated fertilizer of the present invention may also be applied in a single application to supply nitrogen at a rate and timing of release essentially the same as provided by separate applications of fertilizer prescribed under a standard intensive cereal management program (ICM) thereby eliminating the need for multiple fertilizer applications which would otherwise be required by such an ICM program.

In view of the foregoing, it is believed that the ionically and covalently crosslinked sulfonated polymer or interpolymer complex coating of fertilizers in accordance with the present invention, and particularly phosphate fertilizers, would effectively reduce the chemical immobilization of phosphorous as calcium or aluminum/iron phosphate, thereby making fertilizer phosphorous more plant available.

In accordance with the present invention, fertilizers and fertilizers/pesticide combinations with thin films or coatings of ionically and covalently crosslinked sulfonated polymers or interpolymer complexes permits the fertilizer to be applied to the soil at a rate which is at least 10% less than a fertilization rate for a fertilizer not coated in accordance with the present invention determined by a standard soil testing method as being required for the particular crop in the soil of the particular region. Although the rate of fertilizer reduction may be as much as about 50% less than the fertilization rate otherwise required, typically the rate is reduced within the range of about 10-20% less than a conventional fertilization rate.

It has been discovered that fertilizers and fertilizer/pesticide combinations coated with thin films of ionically and covalently crosslinked sulfonated polymers or interpolymer complexes experience reduced nitrogen losses. This is particularly true for urea and ammonium sulfate. Conventionally, introgenous fertilizers added to moist soils, i.e., soils where the moisture levels exceed $\frac{2}{3}$ of field capacity, i.e., 22 kPa, are subject to a loss of nitrogen due to a variety of factors including: leaching into ground waters, the denitrification to $N_2O$ and/or $N_2$ gas, volatilization of ammonia gas, and immobilization into the active microbial biomass. It has been discovered that fertilizers coated with thin films of ionically and covalently crosslinked sulfonated polymers and interpolymer complexes in accordance with the present invention experience substantially reduced losses of nitrogen by controlling the release of nitrogen by the coated fertilizer; thus, the amount of fertilizer nitrogen available at any particular time which would be subjected to the previously mentioned deleterious effects is minimized. An advantage of the present invention, therefore, is a reduction in the losses of, for example, ammonical nitrogen by chemical, physical and biological occurrences. Thus, the present invention has been found effective in increasing plant yields because more nitrogen is available for the needs of the plant, while decreasing pollution of ground water with fertilizer-derived nitrates, decreasing destruction of the ozone layer of the atmosphere due to fertilizer-derived $N_2O$, and increasing residual nitrogen to benefit subsequent crops planted during the normal course of agriculture rotation.

DETAILED DESCRIPTION OF THE PREFERRED EMBODIMENT

The following examples will demonstrate the performance of ionically crosslinked sulfonated polymers and interpolymer complexes as barrier coatings as compared to sulfonated polymers and interpolymer complexes which have been both ionically and covalently crosslinked.

EXAMPLE 1

Preparation of Sulfonated EPDM

A sulfonated EPDM terpolymer (TP-320) is prepared by sulfonating a 40 Mooney viscosity at 100° C. EPDM terpolymer (Royalene 521-Uniroyal) which has about 50 weight percent ethylene, about 5 weight percent ENB, with acetyl sulfate and neutralizing with $Zn(Ac)_2$ according to the procedure of U.S. Pat. No. 3,836,511, herein incorporated by reference, thereby producing 10 meq. of zinc sulfonate groups per 100 grams of the EPDM terpolymer and 25 meq. of zinc sulfonated groups per 100 grams of the EPDM terpolymer.

EXAMPLE 2

Preparation of Styrene-4-Vinyl Pyridine Copolymer

A copolymer of styrene-4-vinyl pyridine was prepared via a free radical emulsion copolymerization process. The preparation was conducted as follows:

In a suitable, stirred reaction vessel under a nitrogen blanket the following ingredients were charged:
120 ml distilled water
50 g styrene
3.2 g sodium lauryl sulfate
0.1 g dodecylthiol
0.2 g potassium persulfate
4.7 g 4-vinyl pyridine The polymerization was conducted at 50° C. for 24 hours and the resultant emulsion was fluid and uniform. Three ml of methanol containing 0.1% of hydroquinone was added as an inhibitor and the reaction mixture was precipitated in a large excess of acetone. The precipitate was filtered, then suspended in methanol and blended in a Waring blender to finally disperse the coagulated polymer. The suspension was filtered and dried in a vacuum oven at 60° C. for 24 hours.

The resulting product represented 80% conversion of the reactive monomers and contained 1.68% nitrogen corresponding to 12.5 mole percent 4-vinyl pyridine incorporation.

EXAMPLE 3

Improved Barrier Properties Of Sulfonated Polymer Coatings

A solution of the sulfonated EPDM polymer of Example 1 was prepared for application as a coating solution. The solution cast coating was applied over urea samples in order to measure the barrier properties for urea extraction by water through the thin film coating.

Solution A was prepared by mixing. The solution consisted of 2.5 grams of a zinc sulfo-EPDM similar to the one described in Example 1 (Uniroyal Ionic Elastomer 2560), containing 25 meq. of sulfonated groups per 100 grams of ethylene propylene ethylidenenorbornene terpolymer neutralized with zinc; in 100 grams of a solvent consisting of 97.5% toluene and 2.5% methanol reagent.

To determine the barrier properties of films formed from the solution of the sulfonated EPDM terpolymer, urea slides were coated for immersion tests. The procedures for preparing coated samples of urea slides and conducting immersion tests are described as follows:

Urea samples were prepared by depositing reagent grade urea (Fisher Scientific) over microscope glass slides. This was done by dipping glass slides into molten urea at a temperature of about 135°–145° C., followed by cooling and solidification of the urea layer. The urea layer was built up to about 7 mm by 4 to 5 successive dipping and cooling cycles. These urea samples were then coated by a polymeric film using a second dipping procedure. Urea slides were repeatedly dipped into polymeric solutions, such as those described above, followed by drying in a vacuum oven at 70° C. for about 3 hours. The dipping and drying cycles were repeated until the film thicknesses shown in Table I were obtained.

The barrier properties of the various polymeric films were determined by immersion of each coated urea slide in about 100 g of deionized water at room temperature. The amount of urea released into the water was determined by recovering the urea after evaporating the water. Each sample was initially immersed for one day, followed by immersion in fresh water for three days and for weekly intervals thereafter.

Table I shows that permeabilities of ureas solution extracted from the coated urea slides and immersed in water at room temperature. The permeabilities of the coating materials were determined by applying Fick's law of diffusion at steady state. Fick's law states that:

$$J_m = DA \frac{C}{t}$$

where $J_m$=mass flux (loss) through the film or membrane, A=transport area, C=concentration gradient, t=film or membrane thickness and D=membrane diffusivity constant which is equal to the ratio of permeability (P) over the solubility ratio (K) of urea in the membrane in water.

The performance of the zinc-sulfo-EPDM film was compared with and those that formed from solutions of other commercial coating materials. The first commercial coating solution was a tung oil solution made by Formby of Mississippi at 30 weight percent solids in petroleum distillate. The second commercial coating solution was linseed oil modified polyurethane Type I made by Minwax Paint Co. of New Jersey at 45% solids in petroleum distillate. The two commercial coatings were cured at 70° C. for 48 hours after coating.

The permeability of urea solution through the zinc sulfonated EPDM terpolymer film was found to be about 3 orders of magnitude lower than either that of tung oil or that of polyurethane. Note that tung oil and polyurethane were claimed as release control coatings for water soluble fertilizers (U.S. Pat. Nos. 3,321,298 and 3,223,518).

This Example shows that thin films of zinc sulfonated EPDM terpolymer complex provide a much better barrier than do commercial materials. See Table I.

TABLE I

PERMEABILITY OF UREA SOLUTION FROM COATED UREA SLIDES IN WATER AT ROOM TEMPERATURE

| Sample Number | Coating Material | Ratio wt/wt | Film Thickness Microns | Permeability (P = DK) cm²/sec |
|---|---|---|---|---|
| 141-3 | Tung Oil | — | 75 | $4.3 \times 10^{-9}$ |
| 141-6 | Tung Oil | — | 125 | $7.6 \times 10^{-9}$ |
| 158-4 | Polyurethane | — | 100 | $1.3 \times 10^{-9}$ |
| 158-5 | Polyurethane | — | 40 | $2.1 \times 10^{-9}$ |
| 28-14 | ZSE | — | 10 | $9.6 \times 10^{-13}$ |
| 84-1 | ZSE | — | 25 | $8.6 \times 10^{-13}$ |
| 84-2 | ZSE | — | 30 | $8.6 \times 10^{-13}$ |
| 84-5 | ZSE-SVP | 90/10 | 25 | $1.1 \times 10^{-13}$ |
| 84-6 | ZSE-SVP | 90/10 | 20 | $1.8 \times 10^{-13}$ |
| 127-B10 | ZSE-SVP | 66.6/33.4 | 15 | $2.5 \times 10^{-13}$ |
| 127-C9 | ZSE-SVP | 66.6/33.4 | 15 | $4.0 \times 10^{-13}$ |

EXAMPLE 4

Improved Barrier Properties of an Interpolymer Complex Coating

A solution of an interpolymer complex, Solution A, was prepared for application as a coating solution. The solution cast coating was applied over urea samples in order to measure the barrier properties for urea extraction by water through the thin film coating.

Solution A was prepared by mixing with a magnetic bar stirrer for at least 1 hour, a given weight ratio of Solution B and Solution C which ranges between 2/1 and 9/1, respectively, of B/C. Solution B consisted of 2.5 grams of a zinc sulfo-EPDM similar to the one described in Example 1 (Uniroyal Ionic Elastomer 2560), containing 25 meq. of sulfonated groups per 100 grams of ethylene propylene ethylidenenorbornene terpolymer neutralized with zinc; in 100 grams of Solvent D. Solution C consisted of 2.5 grams of emulsion copolymerized styrene vinylpyridine, similar to the one described in Example 2, (SVP-703) containing about 8 mole percent vinylpyridine and having an intrinsic viscosity in xylene at 25° C. of about 2.6, in 100 grams of Solvent D. Solvent D consisted of 97.5% toluene and 2.5% methanol reagent. Solutions B and C were also prepared by mixing with a magnetic bar stirrer at room temperature until all the polymer was visually dissolved.

To determine the barrier properties of films formed from the solution of the interpolymer complex urea slides were coated for immersion tests. The procedures for preparing coated samples of urea slides and conducting immersion tests were as described in Example 3.

The performance of the interpolymer complex film was compared with that formed from solutions of two commercial coating materials. The procedures for preparing the coatings are described in Example 3. The permeability of urea solution through the interpolymer complex ZSE-SVP film was found to be about 4 orders of magnitude lower than either that of tung oil or that of polyurethane. Note that tung oil and polyurethane and it is 2-8 times lower than that of ZSE film alone. Note that tung oil and polyurethane were claimed as release control coatings for water soluble fertilizers (U.S. Pat. Nos. 3,321,298 and 3,223,518).

This Example shows that thin films of ZSE-SVP interpolymer complex provide a much better barrier than do commercial materials. Moreover, the Example shows an unexpected synergistic result in barrier properties for ZSE-SVP films at a level of about 90/100 ZSE-SVP when compared to the barrier properties of ZSE films alone.

EXAMPLE 5

Figure 1:
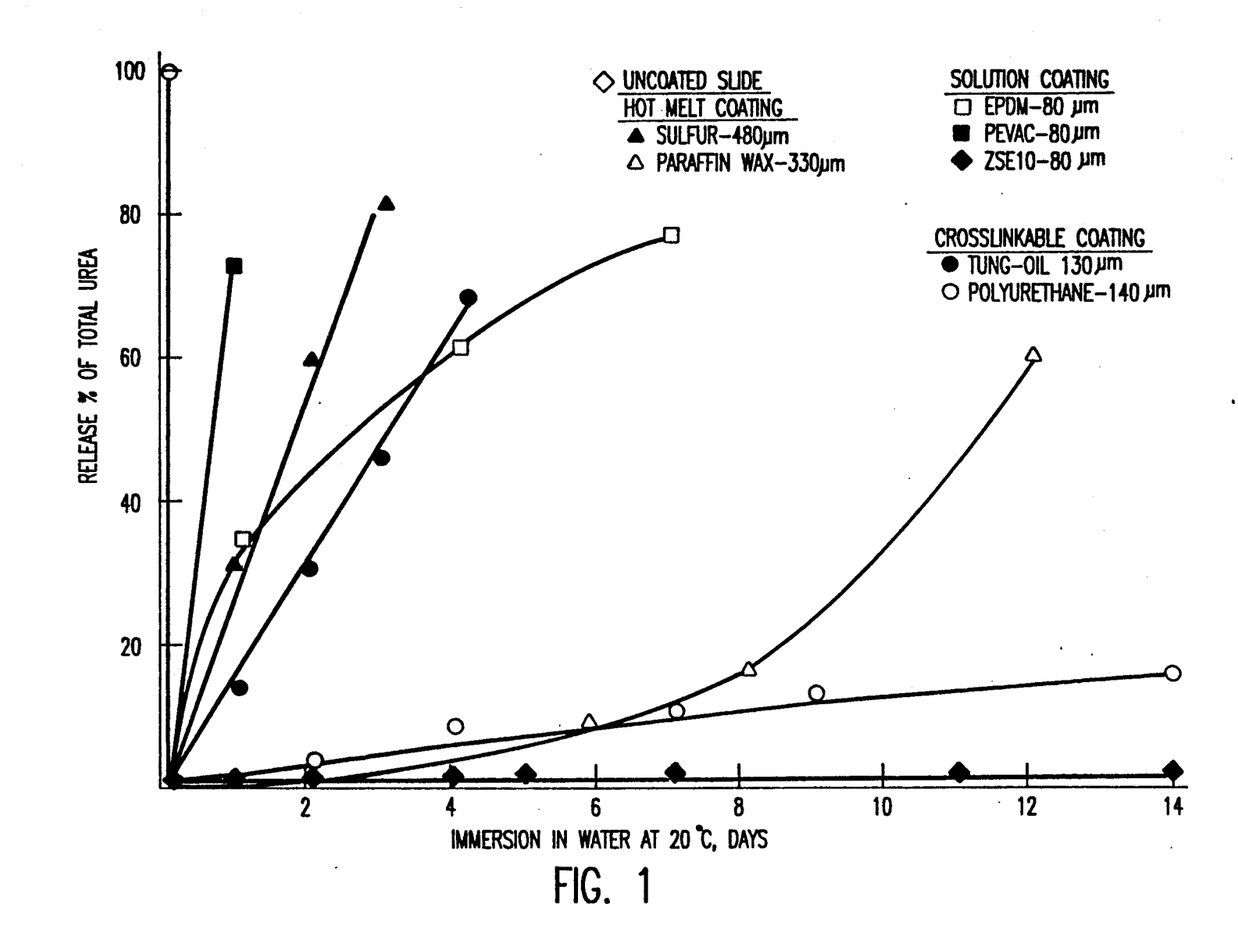
FIG. 1 illustrates urea release versus immersion time in water for the coatings of the instant invention and control samples.

FIG. 1 shows that ZSE-10 offered the best protection in preventing the dissolution of urea in water at room temperature (about 20° C.). Uncoated urea dissolved quickly in water, but even thick coatings of sulfur, unsulfonated EPDM and PEVAC on similar samples did not sufficiently protect urea from dissolving in water. Paraffin wax and modified polyurethane type 1 (made by Minwax Paint Company) protected urea from dissolving in water for at least six days. ZSE-10, however, performed the best in protecting urea from water dissolution. In this Example thick coatings of reagent sulfur and paraffin wax (M.P.=55° C.) were applied through melting (i.e., these materials were melted at about 5° C. to 10° C. above their melting point and then after quickly dipping urea samples in the melt the hot coated sample was brought to room temperature slowly). This layering procedure was repeated three to four times to obtain a thick coating. Both unsulfonated EPDM and PEVAC were applied from 2.5% polymer solution in the same solvent as the solvent for the sulfo EPDM.

EXAMPLE 6

Fluidized Bed Process for SEPDM Coating

The SEPDM coated fertilizer granules were produced using the following procedure:

4 kg of 2 to 3 mm fertilizer granules were introduced into a fluid bed coating machine including a Wurster insert, manufactured by Glatt Air Techniques Inc., model number GPCG-5. The fertilizer was fluidized by blowing 130 scfm of heated air (45° C.) through bed. After the bed reached a temperature of 30° C., a 1.25 weight percent solution of the SEPDM polymer in toluene and methanol cosolvent was sprayed onto the fertilizer granules at the Wurster insert entrance. The spray nozzle used was a commercial two fluid nozzle using air at 3 bars pressure to form an atomized spray regime in the Wurster insert.

The spraying was continued at 40 gm/min rate until the required thickness of polymeric coating was built up on the fertilizer, i.e., approximately 80 minutes per a coating level of 1 wt. % polymer on the fertilizer.

After the solution was sprayed onto the granules in the Wurster insert, the thus coated granules were blown by the heated air upwards into the drying section of the machine. Here, the solvents were evaporated by the hot steam, leaving a thin coat of dried polymeric material on the granules. The dried granules fell back into the fluid bed and then reentered the Wurster insert where the coating process was repeated. Thus, multiple films or layers of the sulfonated polymeric coating was built up until the spraying was stopped.

The spraying was continued until 2 wt. % SEPDM was added. The spraying was stopped and the coated granules were dried with the hot air for 5 minutes. The product was logged and marked 2 wt. % of SEPDM on fertilizer.

EXAMPLE 7

The method for crosslinking the polymer using electron beams was as follows:

Granular fertilizer pellets in the size range of 2 to 3 mm coated with 2 wt. % per Zn sulfo EPDM were placed in a monolayer on a flat bed cart. The cart was placed in an electron beam generator until a dose of 10 Megarads was obtained.

Figure 2:
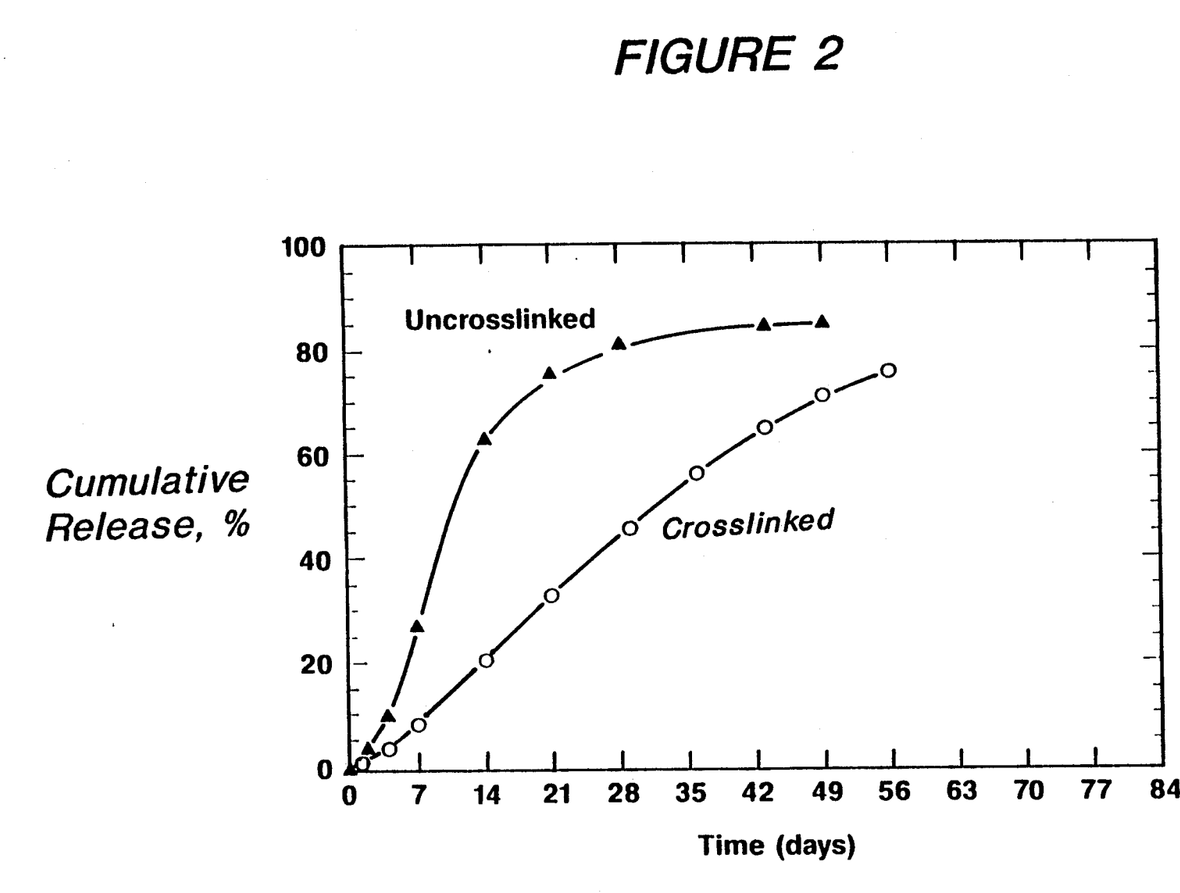
FIG. 2 illustrates release versus immersion time for electron beam (10 Mrads) crosslinked and uncrosslinked Zn sulfor EPDM coated fertilizer.

The results of radiation are shown in FIG. 2. It is seen that electron beam crosslinking significantly reduces the aqueous release rate of these pellets upon immersion in water.

EXAMPLE 8

The method for crosslinking Zn sulfo EPDM with sulfur monochloride was as follows:

Approximately 100 g coated pellets consisting of 2 wt. % Zn sulfo EPDM on 2 to 3 mm granular fertilizer were placed in a monolayer in a flat dish. The dish was then put into a desiccator which contained a separate dish which contained sulfur monochloride. The desiccator was closed and evacuated so that only sulfur monochloride vapor remained. The pellets were left in the desiccator for 24 hours. After that they were removed and placed in a vacuum oven at 40° C. for 10 to 12 hours in order to remove residual sulfur monochloride.

Figure 3:
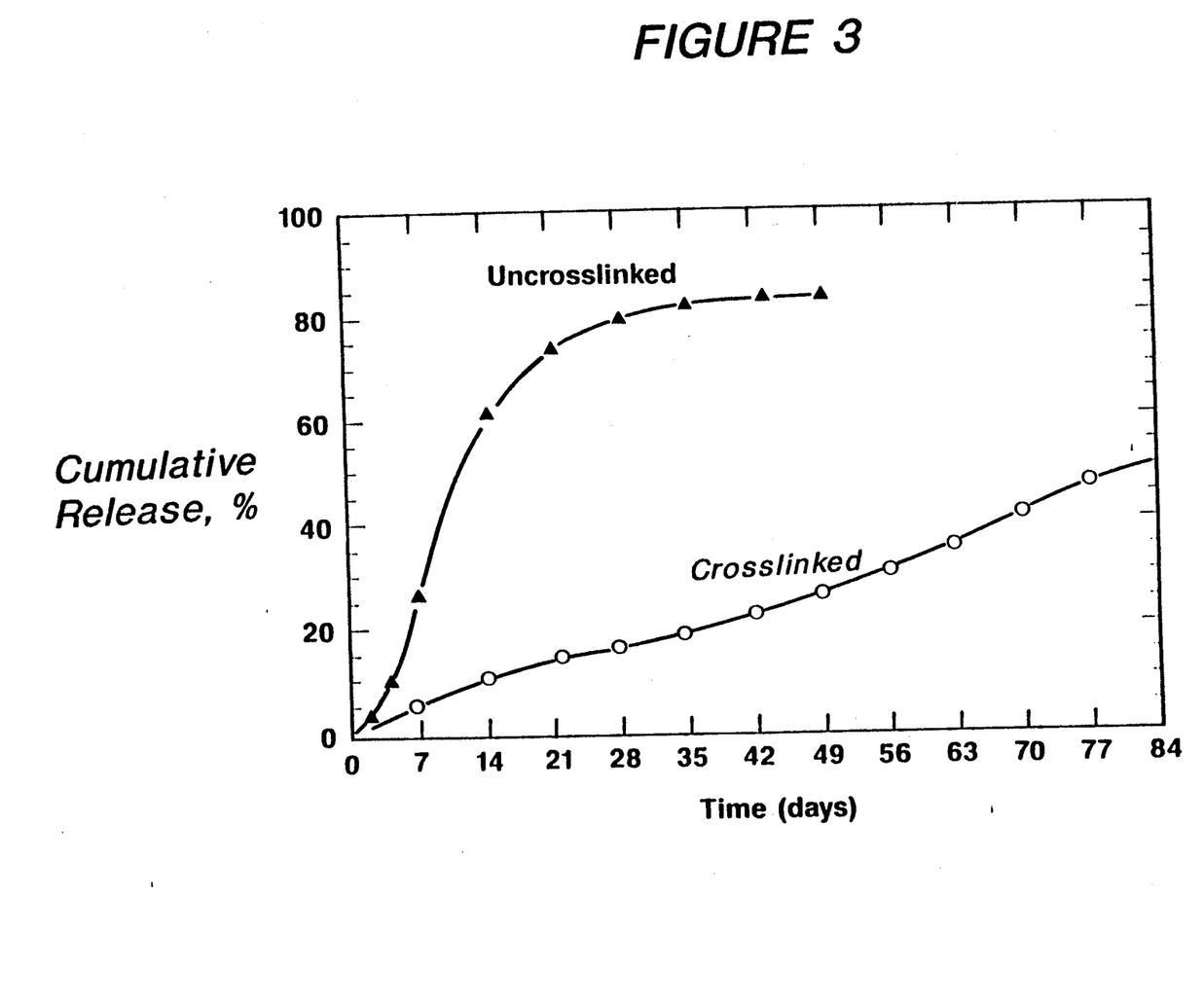
FIG. 3 illustrates aqueous release rates versus immersion time for sulfur monochloride crosslinked and uncrosslinked Zn sulfor EPDM coated fertilizer.

The sulfur monochloride crosslinked and uncrosslinked bare pellets were then placed in water. As shown in FIG. 3, the release rates of the sulfur monochloride crosslinked pellets is much slower than that of the uncrosslinked counterpart.

EXAMPLE 9

The method for crosslinking interpolymer complex coatings on urea slides with sulfur monochloride was as follows:

Dip coated urea slides were prepared with 20 micron thick coatings of polymer complex with B/C solution ratio 2/1 as described in Examples 4 and 5. The slides were then put on a polyethylene screen support in a desiccator which contained a separate dish with 5 ml of sulfur monochloride. The desiccator was closed and evacuated so that only sulfur monochloride vapor remained. The slides were left in the desiccator for 24 hours. After that they were removed and placed in a vacuum oven at 40° C. for 16 hours in order to remove residual sulfur monochloride.

Figure 4:
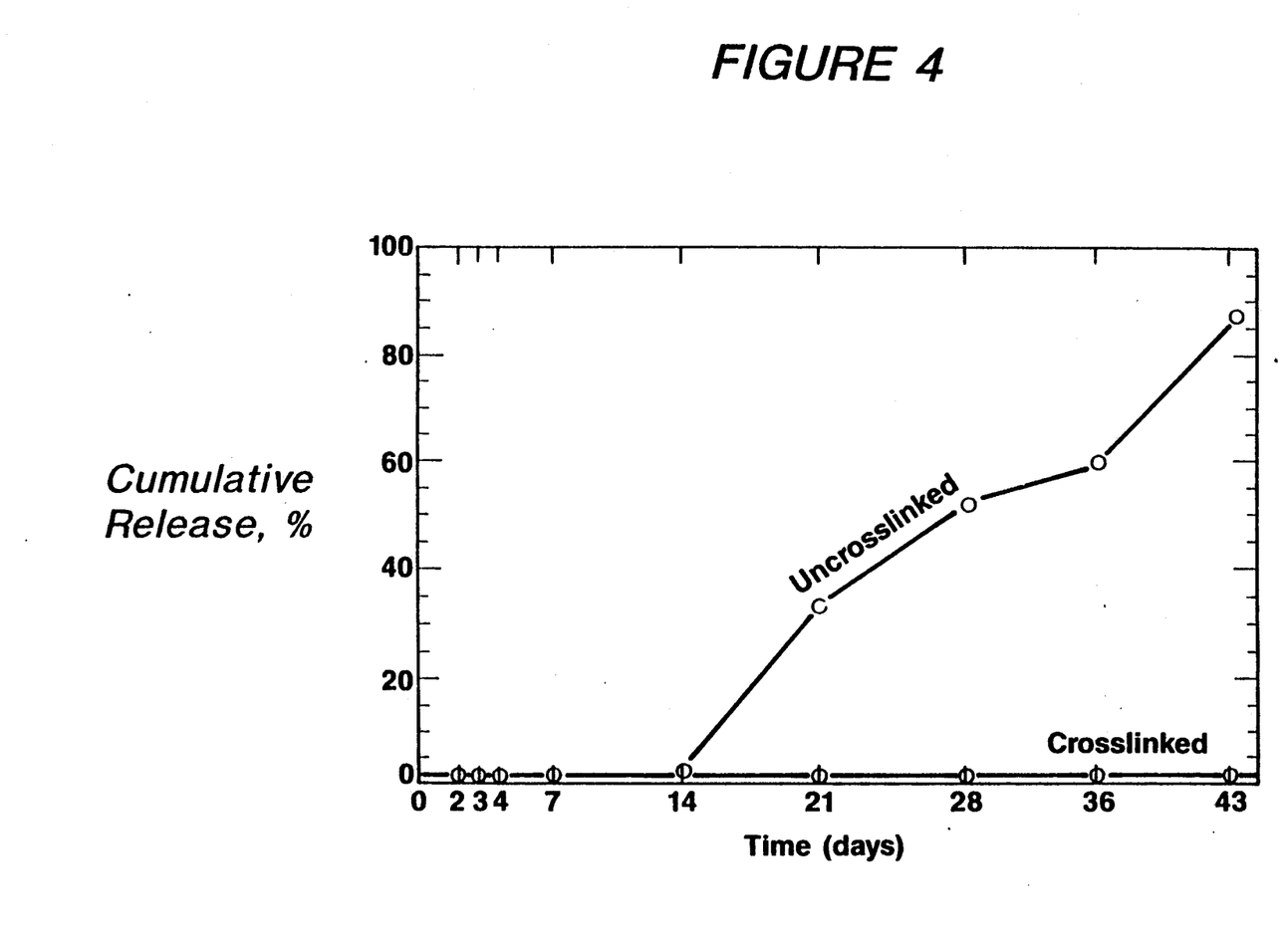
FIG. 4 illustrates aqueous release rates versus immersion time for sulfur monochloride crosslinked and uncrosslinked Zn sulfor EPDM/styrene vinyl pyridine coated fertilizer.

The sulfur monochloride crosslinked and uncrosslinked dip coated slides were then placed in water. As shown in FIG. 4, the release rate of sulfur monochloride crosslinked interpolymer complex coatings was much slower than that of the uncrosslinked counterpart.

What is claimed is:

1. A composite comprising (a) a fertilizer substrate and (b) an ionically and covalently crosslinked, neutralized sulfonic elastomeric coating for said substrate having a thickness of about 1-100 micrometers wherein the elastomeric coating is selected from the group consisting of:

(i) sulfonated polymers having a sulfonate content of about 4-200 meq./100 grams of neutralized sulfonate polymer, and
   (ii) an interpolymeric complex of a sulfonated polymer and an amine containing polymer, having a sulfonate content of about 4-100 meq./100 grams of sulfonated polymer and wherein the nitrogen content of the basic nitrogen atoms ranges from about 4-50 meq./100 grams of amine containing polymer.

2. The composite of claim 1 wherein the coating is (i) or (ii) and the sulfonate groups are neutralized with an ammonium or metal counter ion.

3. The composite of claim 2 wherein the metal counter ion is selected from the group consisting of transition elements and Group IA, IIA, IB, and IIB of the Periodic Chart of the Elements.

4. The composite of claim 3 wherein the sulfonate groups are at least 90% neutralized.

5. The composite of claim 1 wherein the coating is (i) and the sulfonated polymer is EPDM terpolymer or butyl rubber.

6. The composite of claim 1 wherein the coating is (ii) and the sulfonated polymer is EPDM or butyl rubber.

7. The composite of claim 1 wherein the coating is (ii) and the amine containing polymer is a primary, secondary, or tertiary amine.

8. A method for treating a seed or plant which comprises placing in close proximity thereto the composite of claim 1.

9. The method of claim 8 wherein the treat rate exceeds 25 kg/ha.

* * * * *